United States Patent [19]
Jalbert et al.

[11] Patent Number: 5,409,487
[45] Date of Patent: Apr. 25, 1995

[54] AUXILIARY TUBING PROBE

[75] Inventors: Fernand Jalbert; Germain Beland, both of Sherbrooke, Canada

[73] Assignee: Yab Revo-Tech Inc., Ste-Clothilde-de-Horton, Canada

[21] Appl. No.: 187,476

[22] Filed: Jan. 28, 1994

[51] Int. Cl.$^6$ ............................................. A61B 17/39
[52] U.S. Cl. .................................... 606/48; 606/50
[58] Field of Search ................ 606/41, 42, 45, 48, 606/49, 50; 128/642; 607/116, 122, 123

[56] References Cited

U.S. PATENT DOCUMENTS

| | | | |
|---|---|---|---|
| Re. 33,925 | 5/1992 | Bales et al. | 606/48 |
| 3,906,955 | 9/1975 | Roberts | 606/49 |
| 4,608,986 | 9/1986 | Beranek et al. | 607/123 |
| 5,035,695 | 7/1991 | Weber, Jr. et al. | 606/45 |
| 5,092,333 | 3/1992 | Tsuchida et al. | 607/122 |
| 5,197,963 | 3/1993 | Parins | 606/41 |
| 5,277,696 | 1/1994 | Hagen | 606/45 |
| 5,304,176 | 4/1994 | Phillips | 606/41 |
| 5,312,401 | 5/1994 | Newton et al. | 606/42 |

Primary Examiner—Lee S. Cohen
Assistant Examiner—Bua M. Green
Attorney, Agent, or Firm—Robic

[57] ABSTRACT

An auxiliary tubing probe for converting a monopolar electrosurgery probe having a main electrode at one end, into a bipolar electrosurgery probe. The auxiliary probe has an inner electrically insulated tube in which the monopolar electrosurgery probe is slidably inserted. An electric conductor extends externally over and along the inner insulated tube. An auxiliary electrode connected to the electric conductor projects forward away from the inner tube, in such a manner as to be adjacent to the main electrode when the monopolar electrosurgery probe has been inserted in the auxiliary probe. An outer electric insulator covers the electric conductor from the first extremity to the second extremity. The insertion of the auxiliary probe over the monopolar electrosurgery probe, and electricity going through the auxiliary electrosurgery probe and monopolar electrosurgery probe, allows conversion of the monopolar electrosurgery probe into a bipolar electrosurgery probe.

18 Claims, 4 Drawing Sheets

AUXILIARY TUBING PROBE

BACKGROUND OF THE INVENTION a) Field of the Invention

The present invention relates to an auxiliary tubing probe for converting a monopolar electrosurgery probe into a bipolar electrosurgery probe. The expression "electrosurgery probe" as used herein is intended to include all the probes that are or can be used in the medical field, and more particularly for laparoscopy and endoscopy.

b) Description of the Prior Art

Monopolar electrosurgery probes are widely used in laparoscopy and endoscopy, essentially for cutting and healing purposes. They comprise an electrical conducting cannula having one extremity connected to a power source and a second extremity ended by an emitting electrode.

Because of their single polarity, a grounding element is required under or near the patient. Since the grounding element and the emitting electrode are separated by parts of the patient's body, the electric current emitted by the emitting electrode traverses those body parts.

The electric current sometimes causes damages to these body parts, damages that could be avoided by having a nearer grounding element.

SUMMARY OF THE INVENTION

It is therefore the object of the present invention to provide means for easily and temporarily transforming a monopolar electrosurgery probe into a bipolar electrosurgery probe, which thanks to its bipolarity is electrically safer for the patient and the surgeon.

In accordance with the present invention, this object is achieved with an auxiliary tubing probe for converting a monopolar electrosurgery probe into a bipolar electrosurgery probe. The monopolar electrosurgery probe which is of a conventional structure, has a main electrode at one end which is electrically connectable to a power source which generates electricity. The auxiliary probe according to the invention comprises:

- an inner electrically insulated tube in which the monopolar electrosurgery probe may be slidably inserted, the inner tube having first and second ends;
- at least one electric conductor extending externally over and along the inner insulated tube, the electric conductor having a first and a second extremity;
- an auxiliary electrode projecting forward from the first end of the inner tube and being connected to the first extremity of the at least one electric conductor, the auxiliary electrode being adjacent to the main electrode when the monopolar electrosurgery probe has been inserted in the auxiliary probe; and
- an outer electric insulator covering the electric conductor from the first extremity to the second extremity, whereby, insertion of the auxiliary probe over the monopolar electrosurgery probe and electricity going through said auxiliary electrosurgery probe and monopolar electrosurgery probe converts the monopolar electrosurgery probe into a bipolar electrosurgery probe.

Preferably, the auxiliary tubing probe comprises attachment means for retaining it on the monopolar electrosurgery probe.

Preferably also, the auxiliary tubing probe comprises a disengaging flange adjacent to the second end of the inner tube for use to separate it from the monopolar electrosurgery probe.

As aforesaid, the monopolar electrosurgery probe can be a laparoscopic monopolar electrode. It can also be any other kind of electrode used in the medical field.

The objects, advantages and other features of the present invention will become more apparent upon reading of the following non restrictive description of preferred embodiments thereof, given for the purpose of exemplification only, with reference to the accompanying drawings.

DESCRIPTION OF PREFERRED EMBODIMENTS

Figure 1:
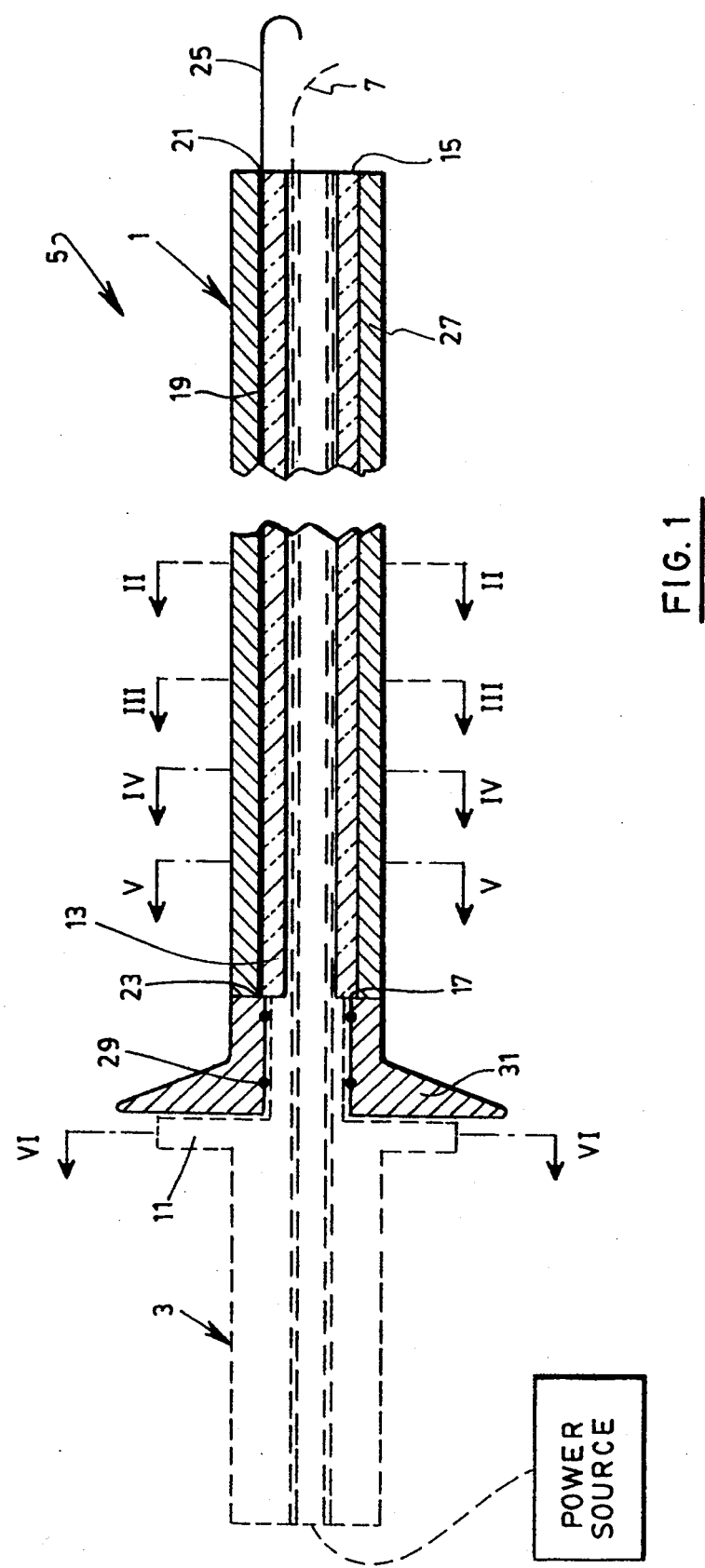
FIG. 1 is an enlarged cross-sectional side elevation view of a conventional monopolar electrosurgery probe shown in dotted lines and provided with an auxiliary tubing probe according to the invention for use to make it bipolar.

Referring to FIG. 1, there is shown an auxiliary tubing probe 1 according to the invention, for converting a monopolar electrosurgery probe 3 shown in dotted lines into a bipolar electrosurgery probe 5.

Figure 6:
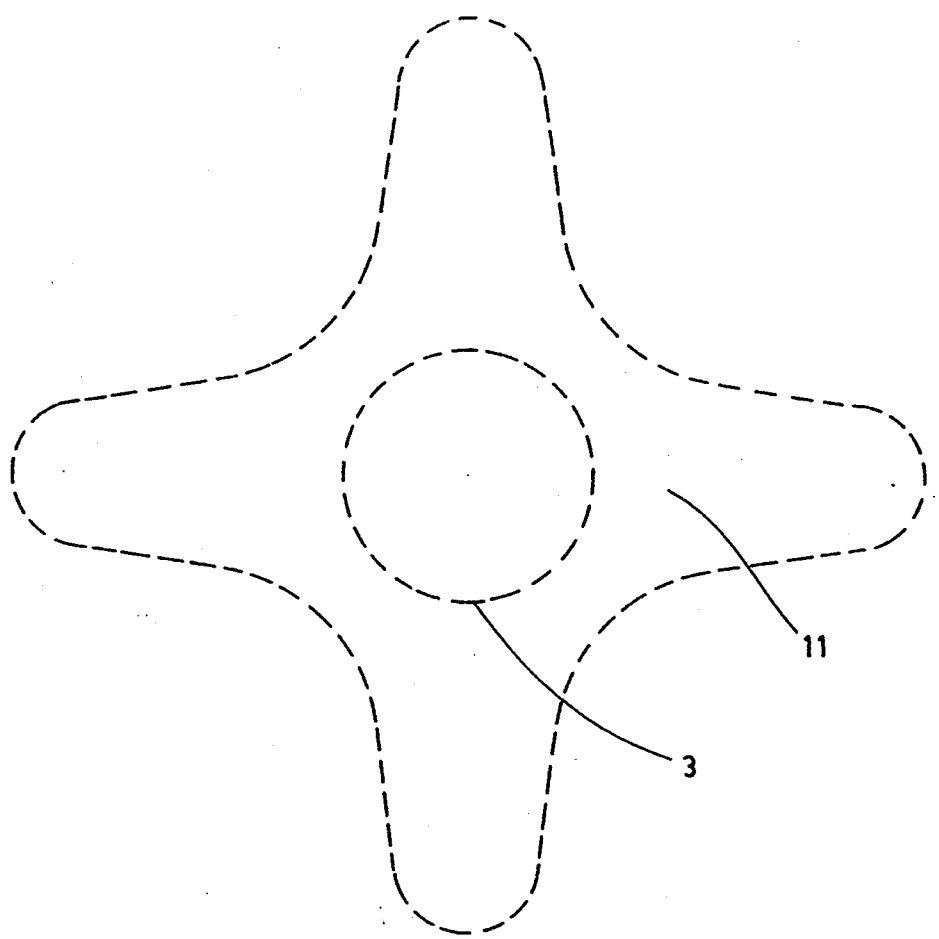
FIG. 6 is an enlarged cross-section on the line VI—VI of FIG. 1 showing the stopping flange of the electrosurgery probe according to the invention.

The monopolar electrosurgery probe 3 preferably consists of a laparoscopic electrode or an electric conducting cannula. The monopolar electrosurgery probe 3 has a main electrode 7 at one end having the shape of a hockey stick, and is electrically connected to a power source 9. The monopolar electrosurgery probe 3 also has a stopping flange 11, for stopping its insertion in the auxiliary probe 1. That stopping flange 11 is star-shaped as shown on FIG. 6.

The auxiliary tubing probe 1 comprises an inner electrically insulated tube 13 in which the monopolar electrosurgery probe 3 is slidably inserted. The inner electrically insulated tube 13 has a first and a second opposite ends 15 and 17. The insulated tube 13 preferably consists of polycarbonate. It may also consist of any material acting as an electric insulator.

Figure 2:
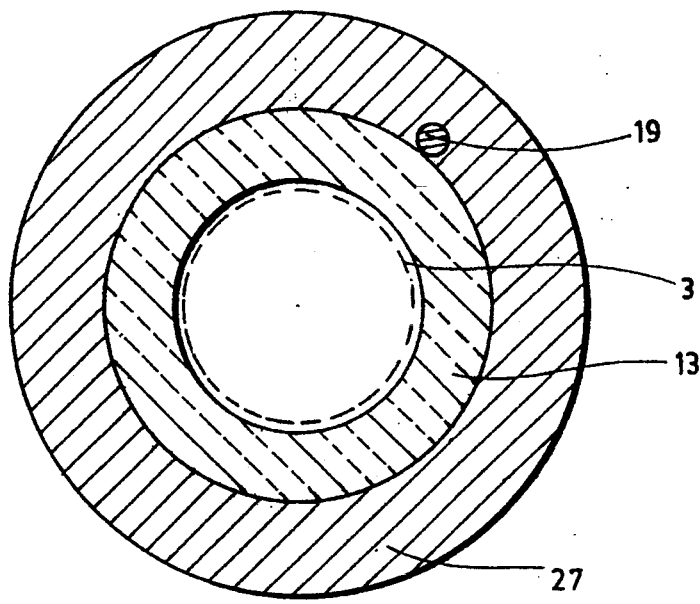
FIG. 2 is an enlarged cross-section on the line II—II of FIG. 1 showing a first preferred embodiment of the invention.

As shown on FIG. 2, at least one electric conductor 19 extends externally over and along the inner insulated tube 13. This electric conductor 19 has a first extremity 21 and a second extremity 23.

The auxiliary tubing probe 1 also comprises an auxiliary electrode 25 projecting forward from the first end 15 of the inner tube 13. The auxiliary electrode 25 preferably has the shape of a J-hook, but may also have the shape of a needle, a hockey stick, a L-hook or a spatula, as is known in this art.

The auxiliary electrode 25 is connected to the first extremity 21 of the at least one electric conductor 19.

When the monopolar electrosurgery probe 3 has been inserted in the auxiliary probe 1, the auxiliary electrode 25 is adjacent to the main electrode 7 of the monopolar electrosurgery probe 3.

The auxiliary tubing probe 1 further comprises an outer electric insulator 27 covering the electrical conductor 19 from its first extremity 21 to its second extremity 23. The outer electric insulator 27 also covers the inner electrically insulated tube 13. The outer electric insulator 27 preferably consists of polycarbonate. It may also consist of any material which is biocompatible and may act as an electrical insulator.

The auxiliary probe 1 also has attachment means for retaining the auxiliary probe 1 on the monopolar electrosurgery probe 3. The attachment means can be of any type but preferably comprises a pair of O-rings 29 mounted in small grooves made in the inner auxiliary probe 1 near the second end 15 of the inner tube 13. The attachment means may also consist in snug-fitting the auxiliary tubing probe 1 over the monopolar electrosurgery probe 3.

The auxiliary probe further comprises a disengaging flange 31 adjacent to the second end 17 of the inner tube 13, used to separate the auxiliary probe 1 from the monopolar electrosurgery probe 3.

Figure 4:
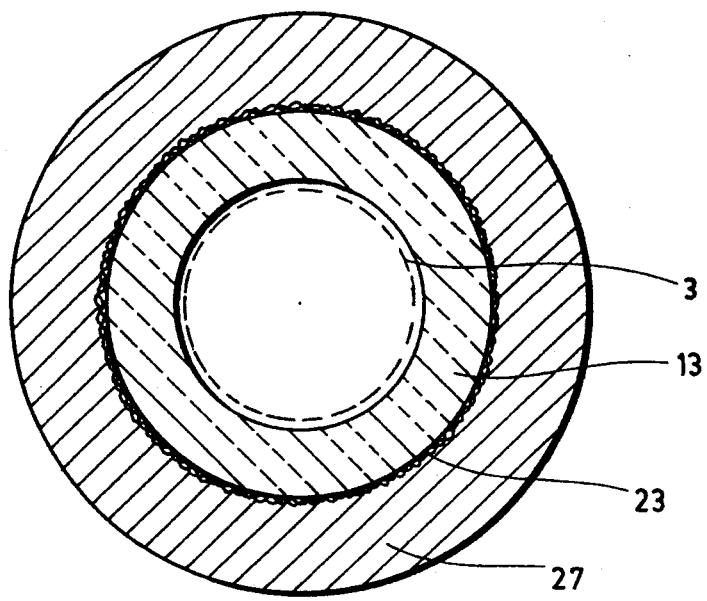
FIG. 4 is an enlarged cross-section on the line II—II of FIG. 1 showing a third preferred embodiment.

In a second embodiment of the invention, shown on FIG. 4, the electrical conductor 19 is a metallic weaver 23 enveloping the inner insulated tube 13. The metallic weaver disposed in such a manner acts as a Faraday cage surrounding the monopolar electrosurgery probe 3. Such a disposition improves the grounding effect of the auxiliary tubing probe 1.

Figure 3:
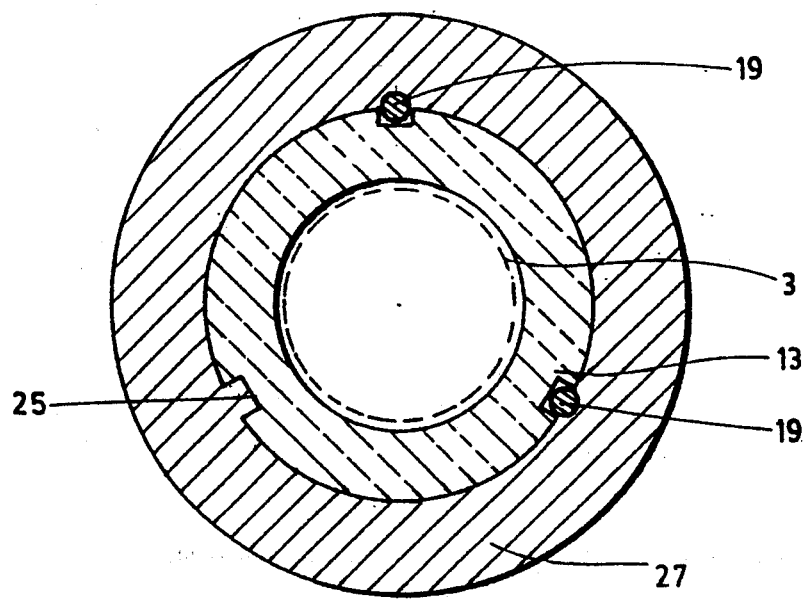
FIG. 3 is an enlarged cross-section on the line II—II of FIG. 1 showing a second preferred embodiment of the invention.

In a third embodiment of the invention, shown on FIG. 3, the at least one electrical conductor 19 is inserted in grooves 25 made in the inner electrically insulated tube 13.

Figure 5:
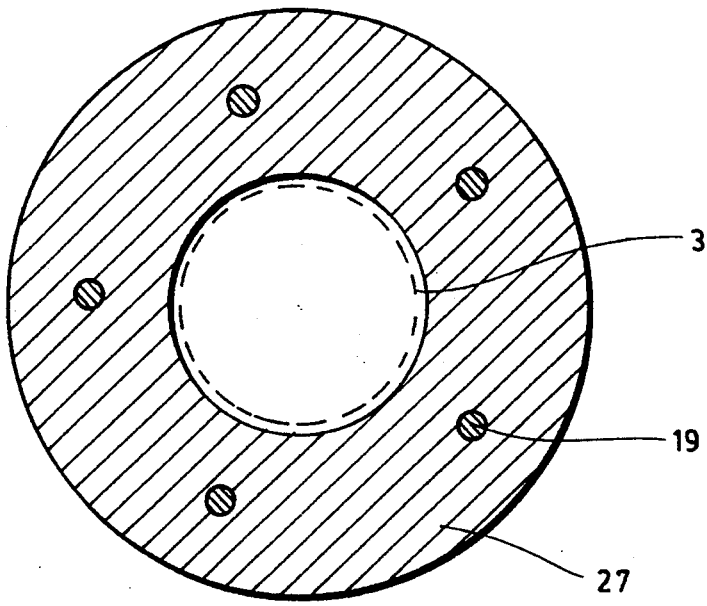
FIG. 5 is an enlarged cross-section on the line II—II of FIG. 1 showing a fourth preferred embodiment.

In a fourth embodiment of the invention, shown on FIG. 5, the outer electric insulator 27 and the inner electrically insulated tube 13 are combined in a single tube into which the at least one electric conductor 19 is inserted.

In use, a first connecting path may consist in connecting the monopolar electrosurgery probe to the power source 9, and to use the auxiliary electrosurgery probe 1 as a floating ground. A second connecting path may be to connect the auxiliary electrosurgery probe 1 to the power source 9 and to use the monopolar electrosurgery probe as a floating ground. A third connecting path may consist in connecting the monopolar electrosurgery probe 3 and the auxiliary electrosurgery probe 1 to the power source 9.

In operation, when the auxiliary tubing probe 1 is inserted over the monopolar electrosurgery probe 3 and when electricity circulates in the probes 1 and 3, the monopolar electrosurgery probe 3 is converted into a bipolar electrosurgery probe 5.

The auxiliary tubing probe easily and temporarily transforms a monopolar electrosurgery probe in a bipolar electrosurgery probe which is electrically safe for both the patient and the surgeon.

Although the present invention has been explained hereinabove by way of preferred embodiments thereof, it should be pointed out that any modifications to these preferred embodiments, within the scope of the appended claims are not deemed to change or alter the nature and scope of the present invention.

I claim:

1. An auxiliary tubing probe for converting a monopolar electrosurgery probe into a bipolar electrosurgery probe, said monopolar electrosurgery probe having a main electrode at one end which is electrically connectable to a power source, said power source generating electricity, said auxiliary probe comprising:

an inner electrically insulated tube in which said monopolar electrosurgery probe may be slidably inserted, said inner tube having first and second opposite ends;

at least one electric conductor extending externally over and along said inner insulated tube, said electric conductor having a first and a second extremity;

an auxiliary electrode projecting forward from the first end of said inner tube and being connected to the first extremity of said at least one electric conductor, said auxiliary electrode being adjacent to said main electrode when said monopolar electrosurgery probe has been inserted in said auxiliary probe;

an outer electric insulator covering said at least one electric conductor from said first extremity to said second extremity; and attachment means for retaining said auxiliary probe on said monopolar electrosurgery probe, whereby, insertion of said auxiliary probe over the monopolar electrosurgery probe and electricity going through said auxiliary electrosurgery probe and monopolar electrosurgery probe converts said monopolar electrosurgery probe into a bipolar electrosurgery probe.

2. An auxiliary probe according to claim 1 further comprising a disengaging flange connected adjacent to the second end of the inner tube for use to separate said auxiliary probe from said monopolar electrosurgery probe.

3. An auxiliary probe according to claim 1 wherein said attachment means are a pair of O-rings mounted in small grooves in an inner portion of said auxiliary probe near the second end of said inner tube.

4. An auxiliary tubing probe for converting a monopolar electrosurgery probe into a bipolar electrosurgery probe, said monopolar electrosurgery probe having a main electrode at one end which is electrically connectable to a power source, said power source generating electricity, said auxiliary probe comprising:

an inner electrically insulated tube in which said monopolar electrosurgery probe may be slidably inserted, said inner tube having first and second opposite ends;

at least one electric conductor extending externally over and along said inner insulated tube, said electric conductor having a first and a second extremity;

an auxiliary electrode projecting forward from the first end of said inner tube and being connected to the first extremity of said at least one electric conductor, said auxiliary electrode being adjacent to said main electrode when said monopolar electrosurgery probe has been inserted in said auxiliary probe;

an outer electric insulator covering said at least one electric conductor from said first extremity to said second extremity; and a disengaging flange connected adjacent to the second end of the inner tube for use to separate said auxiliary probe from said monopolar electrosurgery probe, whereby, insertion of said auxiliary probe over the monopolar electrosurgery probe and electricity going through said auxiliary electrosurgery probe and monopolar electrosurgery probe converts said monopolar electrosurgery probe into a bipolar electrosurgery probe.

5. An auxiliary tubing probe for converting a monopolar electrosurgery probe into a bipolar electrosurgery probe, said monopolar electrosurgery probe having a main electrode at one end which is electrically connectable to a power source, said power source generating electricity, said auxiliary probe comprising:
- an inner electrically insulated tube in which said monopolar electrosurgery probe may be slidably inserted, said inner tube having first and second opposite ends;
- at least one electric conductor extending externally over and along said inner insulated tube, said electric conductor having a first and a second extremity and consisting of a metallic weaver enveloping said inner insulated tube;
- an auxiliary electrode projecting forward from the first end of said inner tube and being connected to the first extremity of said at least one electric conductor, said auxiliary electrode being adjacent to said main electrode when said monopolar electrosurgery probe has been inserted in said auxiliary probe; and
- an outer electric insulator covering said at least one electric conductor from said first extremity to said second extremity, whereby, insertion of said auxiliary probe over the monopolar electrosurgery probe and electricity going through said auxiliary electrosurgery probe and monopolar electrosurgery probe converts said monopolar electrosurgery probe into a bipolar electrosurgery probe.

6. An auxiliary probe according to claim 5 wherein said auxiliary electrode has the shape of a J-hook and said main electrode has the shape of a hockey stick.

7. An auxiliary probe according to claim 5 wherein said inner insulated tube and said outer electric insulator are made of polycarbonate.

8. An auxiliary probe according to claim 5 wherein the first extremity of said at least one electric conductor projects outwardly from said first end of said inner electrically insulated tube.

9. An auxiliary probe according to claim 5 further comprising attachment means for retaining said auxiliary probe on said monopolar electrosurgery probe.

10. An auxiliary probe according to claim 9 further comprising a disengaging flange connected adjacent to the second end of the inner tube for use to separate said auxiliary probe from said monopolar electrosurgery probe.

11. An auxiliary probe according to claim 9 wherein said attachment means are a pair of O-rings mounted in small grooves made in an inner portion of said auxiliary probe near the second end of said inner tube.

12. The combination of an auxiliary tubing probe with a monopolar electro-surgery probe, said monopolar electrosurgery probe having a main electrode at one end which is electrically connectable to a power source, said power source generating electricity, said auxiliary probe comprising:
- an inner electrically insulated tube in which said monopolar electrosurgery probe is slidably inserted, said inner tube having first and second opposite ends;
- at least one electric conductor extending externally over and along said inner insulated tube, said electric conductor having a first and a second extremity and consisting of a metallic weaver enveloping said inner insulated tube;
- an auxiliary electrode projecting forward from the first end of said inner tube and being connected to the first extremity of said at least one electric conductor, said auxiliary electrode being adjacent to said main electrode when said monopolar electrosurgery probe is inserted in said auxiliary probe; and
- an outer insulator covering said at least one electric conductor from said first extremity to said second extremity,
- whereby, insertion of said auxiliary probe over the monopolar electrosurgery probe, and electricity going through said auxiliary electrosurgery probe and monopolar electrosurgery probe converts said monopolar electrosurgery probe into a bipolar electrosurgery probe.

13. The combination according to claim 12 wherein said monopolar electrosurgery probe has a stopping flange for stopping its insertion in said auxiliary probe.

14. The combination according to claim 13 wherein said stopping flange is star-shaped.

15. The combination according to claim 12 wherein said monopolar electrosurgery probe is a laparoscopic monopolar electrode.

16. The combination according to claim 15 wherein said laparoscopic monopolar electrode is an electricity conducting cannula.

17. The combination according to claim 12 wherein:
- said monopolar electrosurgery probe is a laparoscopic monopolar electrode;
- said auxiliary electrode has the shape of a J-hook and said main electrode has the shape of a hockey stick;
- said inner insulated tube and said outer electrical insulator are made of polycarbonate; and
- said monopolar electrosurgery probe has a star-shaped stopping flange.

18. The combination according to claim 17 further comprising:
- a pair of O-rings mounted in small grooves made in an inner portion of said auxiliary probe near the second end of the inner tube; and
- a disengaging flange connected adjacent to the second end of said inner tube for use to separate said auxiliary probe from said monopolar electrosurgery probe.

* * * * *